United States Patent

Doehling et al.

[11] Patent Number: 5,961,667
[45] Date of Patent: Oct. 5, 1999

[54] DYEING HAIR WITH COMPOSITIONS WHICH CONTAIN OXIDATION DYE PRECURSOR COMPOUNDS, ALKALINE EARTH METAL PEROXIDES AND INORGANIC OR ORGANIC ACIDS

[75] Inventors: Annelie Doehling, Muenster; Dirk Lauscher, Ober-Ramstadt, both of Germany

[73] Assignee: Wella AG, Darmstadt, Germany

[21] Appl. No.: 09/015,997

[22] Filed: Jan. 30, 1998

[30] Foreign Application Priority Data

Feb. 15, 1997 [DE] Germany ............... 197 05 875

[51] Int. Cl.⁶ ............................................. A61K 7/13
[52] U.S. Cl. .................. 8/408; 8/406; 8/407; 8/409; 8/410; 8/411; 8/412
[58] Field of Search .................. 8/406, 407, 408, 8/409, 410, 411, 412, 431, 111; 252/186.43

[56] References Cited

U.S. PATENT DOCUMENTS

| 3,861,868 | 1/1975 | Milbrada | 8/410 |
| 4,208,183 | 6/1980 | Grollier et al. | 8/409 |
| 4,925,655 | 5/1990 | Smigel et al. | 424/52 |
| 4,992,077 | 2/1991 | Tennigkeit et al. | 8/406 |
| 5,100,436 | 3/1992 | Wenke | 8/405 |

FOREIGN PATENT DOCUMENTS 4217920  12/1993  Germany .

*Primary Examiner*—Caroline D. Liott
*Attorney, Agent, or Firm*—Michael J. Striker

[57] ABSTRACT

A new oxidizing agent composition for mixing with oxidation dye pre-cursor compounds, such as developer and coupler substances, to form a ready-to-use dye mixture for dyeing keratin fibers is described. The oxidizing agent composition contains from 0.01 to 25 percent by weight of at least one alkaline earth peroxide, based on the ready-to-use dye mixture, and from 0.01 to 25 percent by weight of at least one inorganic or organic acid, salt of the at least one organic or inorganic acid or mixture of the salt and/or the at least one acid, based on the ready-to-use dye mixture.

13 Claims, No Drawings

DYEING HAIR WITH COMPOSITIONS WHICH CONTAIN OXIDATION DYE PRECURSOR COMPOUNDS, ALKALINE EARTH METAL PEROXIDES AND INORGANIC OR ORGANIC ACIDS

BACKGROUND OF THE INVENTION

The subject matter of the present invention is a composition for oxidative dyeing of keratin fibers, particularly human hair, which contains at least one alkaline earth peroxide as oxidizing agent or a combination of at least one alkaline earth peroxide and at least one inorganic or organic acid and/or its salt, as well as a method of oxidative dyeing of keratin fibers using the at least one alkaline earth peroxide as oxidizing agent.

Generally either direct-dyeing dye compounds, or oxidative dye compositions which are produced by oxidative coupling of one or more developer ingredients with one or more coupler ingredients, are used for dyeing keratin-containing fibers, for example wool, fur, feathers and especially human hair. Direct-dyeing dye compounds are applied of course under relatively safe conditions, however direct-dyeing dye compounds have only insufficient fastness properties. Usually intense dyeing with good fastness properties may be obtained with oxidative dye compounds. The color of the dyed fiber is developed however under the influence of comparatively strong oxidizing agents, such as hydrogen peroxide, which frequently causes damage to the fiber being dyed. The use of easily dissolved alkali peroxides and alkali hyperoxides as oxidizing agents is described in German Published Patent application DE-OS 44 45 282, however strongly basic and soluble alkali hydroxides, which similarly cause damage to keratin-containing fibers, arise in the vigorous reaction of this peroxide with water. A process for dyeing hair is described in German Published Patent Application DE-OS 36 28 398, in which the coupling reaction is activated so that it runs sufficiently quickly under weakly alkaline reaction conditions by pre-treatment of the fibers with a greatly diluted transition metal salt solution and/or introduction of a reduced amount of transition metal salts in the hair dye composition. Of course the heavy metal ions enter the keratin fibers so that damage to the hair can occur on repeated treatments. A disadvantage of all the above-mentioned oxidizing agents is that they are present at higher concentration at the beginning of their use and these concentrations decrease during the course of the hair treatment.

SUMMARY OF THE INVENTION

It is an object of the present invention to provide an improved method for oxidative dyeing of keratin fibers, which does not have the above-described disadvantages.

It is a further object of the present invention to provide improved compositions for oxidative dyeing of keratin fibers, which do not have the above-described disadvantages.

It was surprisingly found that the above-described disadvantages could be avoided when an alkaline earth peroxide was used as an oxidizing agent for oxidative hair dye compositions so that it is not necessary to admix hydrogen peroxide solution. Alkaline earth peroxides are poorly soluble compounds, which have an outstanding stability. The concentration of the reactive alkaline earth peroxide in the ready-to-use hair dye composition is nearly constant during the entire application time because of the poor solubility of the compound.

According to the invention, the composition for oxidative dyeing of keratin fiber, especially human hair, contains at least one alkaline earth peroxide, preferably magnesium peroxide, calcium peroxide, barium peroxide and/or strontium peroxide, especially calcium peroxide and/or barium peroxide.

Furthermore it was also surprisingly found that addition of inorganic or organic acids to the hair dye composition containing the at least one alkaline earth peroxide results in a clearly improved dyed color intensity.

Accordingly in a preferred embodiment the composition for oxidative dyeing of keratin fibers, especially human hair, according to the invention contains at least one organic or inorganic acid in addition to the alkaline earth peroxide.

The following acids can be used as the inorganic acid in the composition according to the invention: hydrochloric acid, sulfuric acid and phosphoric acid or their alkali salts and ammonium salts, especially buffering salts, such as sodium hydrogen sulfate, potassium hydrogen sulfate or ammonium hydrogen sulfate, diammonium sulfate, sodium dihydrogen phosphate, potassium dihydrogen phosphate or ammonium dihydrogen phosphate, disodium hydrogen phosphate, dipotassium hydrogen phosphate or diammonium hydrogen phosphate and ammonium chloride.

The following acids can be used as the organic acid in the composition according to the invention: monocarboxylic acids, such as acetic acid, propionic acid or palmitic acid; polycarboxylic acids and dicarboxylic acids, such as oxalic acid, malonic acid or phthalic acid; amino acids, such as glycine, alanine, leucine or amino acids with additional functional groups, such as serine, cysteine, lysine, arginine, ornithine, citrulline or carnitine; aminopolycarboxylic acids, such as nitrilotriacetic acid, β-alaninediacetic acid, serine diacetic acid, isoserinediacetic acid, asparaginediacetic acid, polyasparagine acid, imidodisuccinate, iminodiacetic acid, methyliminodiacetic acid, hydroxyethylethylenediamine triacetic acid, ethylenediaminetetraacetic acid or diethylenetriaminepentaacetic acid; phosphonic acids, such as acetophosphonic acid, hydroxyphosphonic acids and aminophosphonic acids, especially with several phosphonic acid groups, such as 1-hydroxyethane-1,1-diphosphonic acid, aminotri(methylenephosphonic acid), alkylenediaminotetra-(methylenephosphonic acid) and dialkylenetriaminopenta(methylenephosphonic acid), wherein the alkylenes can be ethylene, 1,2-propylene and 1,3-propylene as well as 1,2-butylene and 1,4-butylene; sulfonic acids, such as toluene-sulfonic acid; aminosulfonic acids, such as sulfanilic acid; monohydroxycarboxylic acids or polyhydroxycarboxylic acids, especially α-hydroxycarboxylic acids, such as glycolic acids, lactic acids, gluconic acids and other sugar acids, malic acid, tartaric acid, citric acid or mucic acid as well as alkali salts and ammonium salts of these organic acid, especially buffering salts, such as sodium acetate, potassium acetate or ammonium acetate, sodium oxalate, potassium oxalate or ammonium oxalate; alkali salts of the above-mentioned phosphonic acids and sulfonic acids; alkali salts of the hydroxyphosphonic acids, the alkali salts of aminophosphonic acids, and the alkali salts of aminopolycarboxylic acids, such as diammonium tartrate, disodium tartrate, dipotassium tartrate or potassium/sodium tartrate, potassium hydrogen phthalate, potassium hydrogen tartrate, sodium gluconate, sodium dihydrogen citrate, potassium dihydrogen citrate, ammonium dihydrogen citrate, disodium hydrogen citrate, dipotassium hydrogen citrate, diammonium hydrogen citrate, trisodium citrate, tripotassium citrate and magnesium citrate as well as combinations of these substances. Here the α-hydroxycarboxylic acids, such as citric acid, malic acid and tartaric acid, or their combinations as well as their salts are particularly preferred.

The above-mentioned inorganic and organic acids can be used both alone and also in combination with each other.

Both the solubility equilibrium and the activity of the alkaline earth peroxide is thus controlled by the acid added, and also the pH of the dye preparation is controlled, so that the keratin fibers are dyed under very mild conditions.

The pH value of the ready-to-use dye preparation is approximately in a range of from 4 to 11, preferably from 7 to 10, especially preferably from 7.7 to 9.3.

The alkaline earth peroxide is used in a total amount of from 0.01 to 25 percent by weight, preferably in a total amount of from 0.10 to 10 percent by weight, especially preferably from 0.5 to 5 percent by weight, in the ready-to-use oxidation dye preparation.

The inorganic or organic acids and their salts or combinations are added to the ready-to-use oxidation dye preparation in amounts of from 0.01 to 25 percent by weight, preferably from 0.1 to 15 percent by weight. A total amount of 0.2 to 7.5 percent by weight of the inorganic or organic acids and their salts or combinations is a particularly preferred in the ready-to-use dye preparation.

Conventional oxidation dye pre-cursor compounds may be coupled with each other without addition of the otherwise required hydrogen peroxide solution and/or hydrogen peroxide addition compounds using the above-described oxidizing agent (especially a combination of magnesium peroxide, calcium peroxide, barium peroxide and/or strontium peroxide with an organic and/or inorganic acid).

The following conventional developer and coupler substances may be used as the oxidation dye pre-cursor compounds.

As developer substances the following can be used: standard primary aromatic amines with an additional free or substituted hydroxy or amino group substituent in the ortho- or para-position, indole derivative compounds or substituted heterocyclic compounds, especially from the classes of pyrimidines and pyrazoles, such as 1,4-diaminobenzene (p-phenylendiamine), 1,4-diamino-2-methylbenzene (p-toluylene-diamine), 1,4-diamino-2,6-dimethylbenzene, 1,4-diamino-2,5-dimethylbenzene, 1,4-diamino-2,3-dimethylbenzene, 1,4-diamino-2-chlorobenzene, 4-di[(2-hydroxyethyl)amino]aniline, 4-[(2-methoxyethyl)amino] aniline, 1,4-diamino-2-(2-hydroxy-ethyl)-benzene, 1,3-bis-[N-(2-hydroxy-ethyl)-N-(4-amino-phenyl)-amino-2-propanol, 2',2-[1,2-ethanediyl-bis(oxy-2,1-ethanediyloxy)]-bis-1,4-diaminobenzene, 4-amino-phenol, 4-amino-3-methylphenol, 4-methylaminophenol, 4-amino-2-(aminomethyl)phenol, 4-amino-2-[(2-hydroxyethyl)amino]-methylphenol, 4-amino-2-(methoxymethyl)-phenol, 5-amino-salicylic acid, 2,4,5,6-tetraaminopyrimidine, 2,5,6-tri-amino-4-hydroxy-pyrimidine, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 4,5-diamino-1-[(4-chloro-phenyl)methyl]-1H-pyrazole, 4,5-diamino-1-methylpyrazole, 2,5-dimethylpyridine, 2-amino-6-methylphenol or 2-amino-5-methyl-phenol, alone or in combination with each other.

As the coupler substance conventional substituted m-diaminobenzenes, m-aminophenol, resorcinol derivative compounds, indole derivative compounds, naphthols or substituted heterocyclic compounds can be used, especially from the classes of pyrimidines and pyridines, such as N,N-dimethyl-3-ureidoaniline, 2,6-diamino-pyridine, 2-amino-4-[(2-hydroxyethyl)amino]anisole, 2,4-diamino-1-fluoro-5-methyl-benzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di-[(2-hydroxyethyl)amino]-1,5-dimethoxy-benzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 3-di-[(2-hydroxyethyl)-amino]aniline, 4-amino-l-ethoxy-2-di-[(2-hydroxyethyl)amino]-benzene, 5-methyl-2-(l-methylethyl)phenol, 3-[(2-hydroxy-ethyl)amino]aniline, 3-[(2-aminoethyl)amino]aniline, 1,3-di-(2,4-diaminophenoxy)propane, 2,4-dimethoxy-1,3-diaminobenzene, 2,6-bis-(2-hydroxyethyl)aminotoluene, 3-dimethyl-aminophenol, 5-amino-2-methyl-phenol, 5-amino-4-fluoro-2-methylphenol, 5-amino-4-methoxy-2-methyl-phenol, 5-amino-4-ethoxy-2-methyl-phenol, 3-amino-2,4-dichlorophenol, 3-diethylaminophenol, 3-amino-2-chloro-6-methyl-phenol, 3-aminophenol, 3-[(amidomethyl)amino]phenol, 5-[(2-hydroxy-ethyl)amino]-2-methyl-phenol, 3-[(2-Hydroxyethyl)amino]-phenol, 5-amino-2-ethylphenol, 5-[(3-hydroxypropyl)amino]-2-methylphenol, 3-[(2,3-dihydroxypropyl)amino]-2-methyl-phenol, 3-[(2-hydroxy-ethyl)amino]-2-methylphenol, 5-[(2-hydroxyethyl)amino]-1,3-benzodioxole, 1,3-dihydroxybenzene, 4-chloro-1,3-dihydroxybenzene, 1,3-dihydroxy-2-methyl-benzene, 3,4-methylendioxybenzene, 3,4-methylendioxyaniline, 1-hydroxy-6-bromo-3,4-methylendioxybenzene, 5-amino-4-chloro-2-methylphenol, 3,4-diaminobenzoic acid, 6-hydroxy-2H-1,4-benzoxazine, 2,7-dihydroxynaphthalene, 1-naphthol, 1,7-dihydroxynaphthalene, 1,5-dihydroxynaphthalene, 2,6-dihydroxy-4-methylpyridine, 2,6-dihydroxypyridine, 2-methyl-1-naphthol acetate, phenylmethylpyrazolone, 2,6-dihydroxy-3,4-dimethylpyridine, 4-hydroxyindole, 5,6-dihydroxyindole, 5-hydroxyindole, 6-hydroxyindole, 7-hydroxyindole, 2,3-indolidione, 2-amino-3-hydroxypyrimidine or 4,5,6-dihydroxy-indoline, alone or in combination with each other.

The composition according to the invention contains one or more of the previously named developer and coupler substances. These dye compounds, in so far as they are bases can also be used in the form of their physiologically compatible acid addition salts, for example as the hydrochlorides and/or sulfates, or, in so far as they have aromatic OH groups, in the form of salts with bases, for example as alkali phenolates.

The oxidation dye pre-cursor compounds are, based on the ready-to-use dye mixture, contained in the oxidation dye composition according to the invention in a total amount of from 0.02 to 20 percent by weight, preferably in a total amount of from 0.5 to 5 percent by weight. The developer and coupler substances are preferably used in equimolar amounts. It is however not disadvantageous when one of these classes of substances is present in excess with respect to the other, or vice versa. The developer and coupler substance can be present, for example, in a ratio of from 1:0.5 to 1:2.

Also standard direct-dyeing dye compounds, for example triphenylmethane dye compounds, such as Basic Violet 14 (C.I. 42 510) and Basic Violet 2 (C.I. 42 520), aromatic nitro dye compounds, such as 2-amino-4,6-dinitrophenol, 2-nitro-4-(2'-hydroxyethylamino)-aniline and 2-amino-4-nitrophenol; azo dye compounds, such as Acid Brown 4 (C.I. 14 805) and Acid Blue 135 (C.I. 13 385); anthraquinone dye compounds, such as Disperse Violet 4 (C.I. 61 105), Disperse Blue (C.I. 64 500), Disperse Red 15 (C.I. 60710), Disperse Violet 1 (C.I. 61 100), 1,4,5,8- tetraaminoanthraquinone and 1,4-diaminoanthraquinone, can be contained in the oxidation dye composition according to the invention to obtain special color shades or tones.

Alkaline earth peroxides cannot be stored in aqueous solution because of their hydrolytic sensitivity. Formulations, which contain the oxidation system according to the invention, are thus water-free. By "water-free" it is meant that the total amount of the trace moisture contained in the material and/or the water of crystallization in the material used in the dye composition according to the invention (based on the ready-to-use dye mixture) is not greater than 10 percent by weight, advantageously less than 4 percent by weight, especially less than 1 percent by weight.

The oxidizing composition according to the invention (comprising at least one alkaline earth peroxide or a combination of at least one alkaline earth peroxide and at least one organic and/or inorganic acid) is formulated as a mixture with the dye precursor compounds in a water-free medium, preferably in the form of a dust-free powder. This mixture is mixed with water to start the dye reaction immediately prior to use, for example preferably in a weight ratio of 1:0.5 to 1:20. Similarly it is also possible to package the oxidation hair dye composition according to the invention in the form of a 2-component preparation, in which the alkaline earth peroxides are packaged as a water-free formulation in powder form, or microencapsulated, or as a suspension in a water-free medium separately from the conventional ingredients of the oxidation hair dye composition, while the conventional ingredients of the oxidation hair dye composition are present in the form of a aqueous preparation. The oxidizing composition is mixed intimately with the water-containing preparation in this case immediately prior to use. The water-containing preparation can also be present in the form of a concentration, which is diluted with water immediately prior to use.

The oxidation system according to the invention and the dye precursor compounds are worked into the cosmetic preparation individually or as a mixture, which acts as a carrier, in which the alkaline earth peroxides are found in a water-free (according to the above definition) medium.

Suitable cosmetic preparations include, for example, creams, emulsions, gels, surfactant-containing solutions, such as shampoos, foam aerosols or other formulations suitable for hair cosmetic purposes. Convention ingredients of such preparations are described in the professional literature, for example in K. Schrader, "Grundlagen und Rezepturen der Kosmetika (Cosmetic Fundamentals and Formulations)", 2nd Edition, Huthig Verlag, Heidelberg, 1989.

These conventional cosmetic ingredients can include, for example: surfactants and emulsifiers, such as anionic, non-ionic or ampholytic surface-active compounds, such as fatty alcohol sulfates, alkane sulfonates, olefin sulfonates, fatty alcohol polyglycol ether sulfates, alkylpolyglycosides and ethoxylated fatty alcohols, fatty acids, alkylphenols, sorbitan fatty acid esters and fatty acid alkanolamides; thickeners and gel-formers, such as fatty alcohols, fatty acids, paraffin oils, fatty acid esters, methylcelluloses or hydroxyethyl celluloses, starch, synthetic polymerizates, such as polyvinylpyrrolidone(PVP) or polyacrylates, biopolymers, such as alginic acid, antioxidants for stabilizing the dye compounds, such as ascorbic acid, thioglycolic acid or sodium sulfite, as well as complex formers, perfume oils and hair care additives, such as cationic resin, lanolin derivative compounds, cholesterol, pantothenic acid, protein derivative compounds and protein hydrolyzates, pro-vitamins and vitamins and plant extracts.

The ingredients of the cosmetic preparations are used in standard amounts suitable for their purpose to make the hair dye composition according to the invention, for example the emulsifiers are used in concentrations of from 0.2 to 30 percent by weight and the thickeners in concentrations of from 0.1 to 25 percent by weight, based on the total amount of the ready-to-use oxidation hair dye composition.

The method for dyeing hair using the hair dye composition according to the invention includes mixing the individual components with each other immediately prior to use, if necessary with water, and then applying the ready-to-use mixture to the hair in an amount sufficient to dye the hair, preferably from 30 to 150 grams.

The application temperature is in the vicinity of from 10 to 50° C., preferably from 20 to 40° C. The dyeing process can be accelerated by heating during the treatment. The hair dyeing mixture is rinsed thoroughly from the hair with water after an acting time of from 10 to 60 minutes, preferably 30 to 45 minutes, especially preferably 30 minutes at 40° C. and 40 minutes at 20° C. The after-washing with a shampoo can be omitted, if a strong surfactant-containing cosmetic preparation, for example a dyeing shampoo was used.

The oxidation hair dye composition according to the invention permits an exceptionally mild and safe dyeing of the hair, which leads to an outstanding color development without addition of hydrogen peroxide.

The following examples should illustrate the invention in more details without limiting the claims appended hereinbelow.

EXAMPLES

Examples 1 to 40

Hair Dye Solution

| | |
|---|---|
| 0.0025 mol | Developer according to Table I |
| 0.0025 mol | Coupler according to Table I |
| 0.3 g | disodiumethylenediaminotetraacetic acid |
| 0.3 g | ascorbic acid |
| 10.0 g | ethanol |
| 10.0 g | lauryl alcohol diglycol ether sulfate sodium salt (28% aqueous solution) |
| to 100.0 g | water |

Examples 1 to 24

Performing the Hair Dyeing 100 g of the above-described hair dye solution are thoroughly mixed with a mixture of 0.32 g calcium peroxide, 0.12 g calcium hydroxide, 0.06 g calcium carbonate and X g of acid and/or acid salt according to the following Table I. The obtained ready-to-use hair dye composition is applied to the hair and thoroughly rinsed from the hair after an acting time of 30 minutes at 40° C. Subsequently the hair is dried. The resulting colors on bleached hair are summarized with the respective pH values in Table I.

Examples 25 to 33

Performing the Hair Dyeing 100 g of the above-described hair dye solution are thoroughly mixed with a mixture of 0.7 g barium peroxide and X g of acid and/or acid salt according to the following Table I. The obtained ready-to-use hair dye composition is applied to the hair and thoroughly rinsed from the hair after an acting time of 30 minutes at 40° C. Subsequently the hair is dried. The resulting colors on bleached hair are summarized with the respective pH values in Table I.

Examples 34 to 40

Performing the Hair Dyeing 100 g of the above-described hair dye solution are thoroughly mixed with a mixture of 0.25 g magnesium peroxide, 0.68 g magnesium oxide and X g of acid and/or acid salt according to the following Table I. The obtained ready-to-use hair dye composition is applied to the hair and thoroughly rinsed from the hair after an acting time of 30 minutes at 40° C. Subsequently the hair is dried. The resulting colors on bleached hair are summarized with the respective pH values in Table I.

The pH values of exemplary compositions of 33 to 36 in Table I were obtained by adjustment with 25% ammonia solution.

TABLE I

DYE HAIR COLOR AND pH OBTAINED DYEING BLEACHED HAIR
WITH EXAMPLES OF THE COMPOSITION ACCORDING TO THE INVENTION

| No. | Developer | Coupler | Peroxide | acid/salt | pH | Color |
|---|---|---|---|---|---|---|
| 1 | 2,3,4,6-tetraamino-pyrimidine | 2-amino-4-(2-hydroxy-ethyl)aminoanisole | $CaO_2$ | 2 g diammonium-tartrate | 8–8.5 | Blue |
| 2 | 2,3,4,6-tetraamino-pyrimidine | 2-(2,4-diaminophenoxy)-ethanol | $CaO_2$ | 2 g diammonium-tartrate | 8–8.5 | Blue |
| 3 | 2,3,4,6-tetraamino-pyrimidine | 2-hydroxy-4-aminotoluene | $CaO_2$ | 2 g diammonium-tartrate | 8–8.5 | Violet |
| 4 | 2,3,4,6-tetraamino-pyrimidine | 1-naphthol | $CaO_2$ | 2 g diammonium-tartrate | 8–8.5 | turquoise |
| 5 | 2,3,4,6-tetraamino-pyrimidine | 2-methyl resorcinol | $CaO_2$ | 2 g diammonium-tartrate | 8–8.5 | red |
| 6 | 4,5-diamino-1-(2-hydroxyethyl)-pyrazole | 2-amino-4-(2-hydroxy-ethyl)aminoanisole | $CaO_2$ | 2 g carnitine hydrochloride | 4–5 | violet-red |
| 7 | 4,5-diamino-1-(2-hydroxyethyl)-pyrazole | N-aminophenol | $CaO_2$ | 2 g carnitine hydrochloride | 4–5 | red- |
| 8 | 4,5-diamino-1-(2-hydroxyethyl)-pyrazole | 2-hydroxy-4-amino-toluene | $CaO_2$ | 2 g carnitine hydrochloride | 4–5 | orange-red |
| 9 | 4,5-diamino-1-(2-hydroxyethyl)-pyrazole | N-(3-dimethylamino)-phenylurea | $CaO_2$ | 2 g carnitine hydrochloride | 4–5 | blue |
| 10 | 2,5-diamino-toluene | 1,3-diaminobenzene | $CaO_2$ | 0.5 g citric acid | 5–7 | dark blue |
| 11 | 2,5-diamino-toluene | 2-amino-4-(2-hydroxy-ethyl)aminoanisole | $CaO_2$ | 0.5 g citric acid | 5–7 | dark blue |
| 12 | 2,5-diamino-toluene | 2-(2,4-diaminophenoxy)-ethanol | $CaO_2$ | 0.5 g citric acid | 5–7 | blue |
| 13 | 2,5-diamino-toluene | 3-aminophenol | $CaO_2$ | 0.5 g citric acid | 5–7 | red brown |
| 14 | 2,5-diamino-toluene | 4-(2-hydroxyethylamino)-1,2-methylenedioxybenzene | $CaO_2$ | 0.5 g citric acid | 5–7 | dull yellow brown |
| 15 | 2,5-diamino-toluene | 2-hydroxy-4-amino-toluene | $CaO_2$ | 0.5 g citric acid | 5–7 | violet |
| 16 | 2,5-diamino-toluene | 1-naphthol | $CaO_2$ | 0.5 g citric acid | 5–7 | blue |
| 17 | 2,5-diamino-toluene | 2-methyl resorcinol | $CaO_2$ | 0.5 g citric acid | 5–7 | red brown |
| 18 | 2,5-diamino-toluene | N-(3-dimethylamino)-phenylurea | $CaO_2$ | 0.5 g citric acid | 5–7 | blue-green |
| 19 | 2,5-diamino-toluene | 2-amino-4-(2-hydroxy-ethyl)aminoanisole | $CaO_2$ | 5 g ammonium chloride + 2 g glycolic acid | 3–4 | blue |
| 20 | 2,5-diamino-toluene | 2-hydrdxy-4-amino-toluene | $CaO_2$ | 5 g ammonium chloride + 2 g glycolic acid | 3–4 | orange-red |
| 21 | 2,5-diamino-toluene | 2-amino-4-(2-hydroxy-ethyl)aminoanisole | $CaO_2$ | 5 g ammonium chloride + 1 g magnesium citrate | 7–7.5 | intense blue |
| 22 | 2,5-diamino-toluene | 2-hydroxy-4-amino-toluene | $CaO_2$ | 5 g ammonium chloride + 1 g magnesium citrate | 7–7.5 | violet |
| 23 | 2,5-diamino-toluene | 2-amino-4-(2-hydroxy-ethyl)aminoanisole | $CaO_2$ | 3 g ammonium chloride | 8.2 | dark-blue |

TABLE I-continued

DYE HAIR COLOR AND pH OBTAINED DYEING BLEACHED HAIR
WITH EXAMPLES OF THE COMPOSITION ACCORDING TO THE INVENTION

| No. | Developer | Coupler | Peroxide | acid/salt | pH | Color |
|---|---|---|---|---|---|---|
| 24 | 2,5-diamino-toluene | 2-hydroxy-4-amino-toluene | $CaO_2$ | 3 g ammonium chloride | 8.2 | violet |
| 25 | 2-(2-hydroxyethyl)-1,4-diaminobenzene | 1,3-diaminobenzene | $BaO_2$ | 3 g glycine | 8–8.5 | blue |
| 26 | 2-(2-hydroxyethyl)-1,4-diaminobenzene | 2-amino-4-(2-hydroxy-ethyl)aminoanisole | $BaO_2$ | 3 g glycine | 8–8.5 | blue |
| 27 | 2-(2-hydroxyethyl)-1,4-diaminobenzene | 2-(2,4-diaminophenoxy)-ethanol | $BaO_2$ | 3 g glycine | 8–8.5 | blue |
| 28 | 2-(2-hydroxyethyl)-1,4-diaminobenzene | 3-aminophenol | $BaO_2$ | 3 g glycine | 8–8.5 | red-brown |
| 29 | 2-(2-hydroxyethyl)-1,4-diaminobenzene | 4-(2-hydroxyethylamino)-1,2-methylenedioxy-benzene | $BaO_2$ | 3 g glycine | 8–8.5 | dull yellow-brown |
| 30 | 2-(2-hydroxyethyl)-1,4-diaminobenzene | 2-hydroxy-4-amino-toluene | $BaO_2$ | 3 g glycine | 8–8.5 | red-violet |
| 31 | 2-(2-hydroxyethyl)-1,4-diaminobenzene | 1-naphthol | $BaO_2$ | 3 g glycine | 8–8.5 | blue |
| 32 | 2-(2-hydroxyethyl)-1,4-diaminobenzene | 2-methyl resorcinol | $BaO_2$ | 3 g glycine | 8–8.5 | red-brown |
| 33 | 1,4-diamino-benzene | 1,3-diaminobenzene | $MgO_2$ | 2 g acetic acid | 8.5–9 | dark green blue |
| 34 | 1,4-diamino-benzene | 2-amino-4-(2-hydroxy-ethyl)aminoanisole | $MgO_2$ | 2 g acetic acid | 8.5–9 | dark blue |
| 35 | 1,4-diamino-benzene | 2-(2,4-diaminophenoxy)-ethanol | $MgO_2$ | 2 g acetic acid | 8.5–9 | dark blue |
| 36 | 1,4-diamino-benzene | 1-naphthol | $MgO_2$ | 2 g acetic acid | 8.5–9 | blue |
| 37 | 1,4-diamino-benzene | 1,3-diaminobenzene | $MgO_2$ | 2 g acetic acid | 4.5 | gray blue |
| 38 | 1,4-diamino-benzene | 2-amino-4-(2-hydroxy-ethyl)aminoanisole | $MgO_2$ | 2 g acetic acid | 4.5 | blue |
| 39 | 1,4-diamino-benzene | 2-(2,4-diaminophenoxy)-ethanol | $MgO_2$ | 2 g acetic acid | 4.5 | blue |
| 40 | 1,4-diamino-benzene | 1-naphthol | $MgO_2$ | 2 g acetic acid | 4.5 | violet-blue |

Example 41

Dye Composition in the Form of a Gel

| Component A: | |
|---|---|
| 1.1 g | 2,5-diaminotoluene |
| 1.2 g | 4-amino-3-methylphenol |
| 1.2 g | 5-amino-2-methylphenol |
| 1.4 g | 2-amino-4-(2-hydroxyethyl) aminoanisole |
| 0.3 g | ascorbic acid |
| 7.0 g | 2-propanol |
| 15.0 g | oleic acid |
| 10.0 g | ammonia (25% aqueous solution) |
| to 100.0 g | water |

| Component B: | |
|---|---|
| 32.0 g | calcium peroxide |
| 12.0 g | calcium hydroxide |
| 6.0 g | calcium carbonate |
| 50.0 g | diammonium hydrogen carbonate |
| 100.0 g | |

50 g of component A are mixed with 5.0 g of component B immediately prior to use and mixed thoroughly with 50 ml of water. The ready-to-use dye preparation prepared is applied to the hair and after an acting time of 30 minutes and 40° C. rinsed thoroughly with water. Subsequently the hair is dried. The hair has an intense dark violet color after this dyeing process.

Examples 42–64

Dye Composition in the form of a Gel

| Component A: | |
|---|---|
| X g | Dye pre-cursor compounds and direct-dyeing dye compound (according to Table II) |
| 0.3 g | sodium sulfite |
| 0.1 g | ascorbic acid |
| 3.5 g | lauryl alcohol diglycol ether sulfate-sodium salt (28% aqueous solution) |
| 15.0 g | cetyl alcohol |
| 3.0 g | ammonia (25% aqueous solution) |
| to 100.0 g | water |

| Component B: | |
|---|---|
| 32.0 g | calcium peroxide |
| 12.0 g | calcium hydroxide |
| 6.0 g | calcium carbonate |
| 50.0 g | diammonium hydrogen carbonate |
| 100.0 g | |

50 g of component A are mixed with 5.0 g of component B immediately prior to use and mixed thoroughly with 50 ml of water. The resulting ready-to-use dye preparation is allowed to act on blond natural hair for 30 minutes at 40° C. Subsequently the hair is rinsed thoroughly with water and dried. The choice and amount X (in grams) of the hair dye pre-cursor compounds and the resulting color of the dyed hair are tabulated in Table II.

TABLE 2

DYED HAIR COLOR OBTAINED WITH DYE COMPOSITIONS ACCORDING TO THE INVENTION

| Dye Compound/Example | 42 | 43 | 44 | 45 | 46 |
|---|---|---|---|---|---|
| 2,5-diaminotoluene | 0.838 | 0.826 | 0.858 | 0.197 | — |
| 4-amino-3-methylphenol | — | 0.312 | 0.034 | 0.382 | 1.923 |
| resorcinol | 0.311 | 0.402 | 0.204 | 0.197 | — |
| 2-methylresorcinol | 0.108 | — | 0.314 | — | — |
| 3-aminophenol | 0.019 | 0.036 | — | 0.248 | 1.648 |
| 5-amino-2-methylphenol | 0.046 | 0.271 | 0.059 | — | — |
| 2-amino-6-chlor-4-nitrophenol | — | 0.096 | — | — | — |
| 1-naphthol | — | — | — | — | 0.317 |
| Color | chocolate brown | mahogony | ruby red | ruby red | colorado red |

| Dye Compound/Example | 47 | 48 | 49 | 50 | 51 |
|---|---|---|---|---|---|
| 2,5-diaminotoluene | 3.986 | 1.967 | 0.871 | 1.472 | 1.003 |
| 2-amino-5-methylphenol | — | — | — | 0.023 | — |
| resorcinol | 1.494 | 0.723 | 0.407 | 0.478 | 0.366 |
| 2-methyl resorcinol | — | — | 0.017 | 0.288 | 0.114 |
| 3-aminophenol | 0.711 | 0.238 | 0.023 | 0.023 | — |
| 5-amino-2-methylphenol | — | — | — | — | 0.042 |
| 2-amino-4-(2-hydroxyethyl)aminoanisole | 1.413 | — | — | — | — |
| 2-(2,4-diaminophenoxy)-ethanol | — | 0.052 | — | — | — |
| 2-amino-6-chloro-4-nitrophenol | — | — | — | 0.021 | 0.073 |
| Color | deep black | medium brown | dark blond | gold-brown | mahogany copper |

| Dye Compound/Example | 52 | 53 | 54 | 55 | 56 |
|---|---|---|---|---|---|
| 2,5-diaminotoluene | 1.403 | 0.248 | 0.797 | 4.012 | 1.961 |
| 4-amino-3-methylphenol | 0.082 | 1.206 | — | — | — |
| 2-amino-5-methylphenol | 0.042 | 0.352 | — | — | — |
| resorcinol | 0.098 | — | — | 1.504 | 0.723 |
| 2-methylresorcinol | 0.604 | — | — | — | — |
| 3-aminophenol | — | — | — | 0.713 | 0.239 |
| 5-amino-2-methylphenol | 0.108 | 1.097 | 0.506 | — | — |
| 2-amino-4-(2-hydroxyethyl)aminoanisole | 0.082 | — | — | — | — |
| 1,5-bis-(2-hydroxyethoxy)-2,4-diaminobenzene | — | — | — | 1.397 | — |
| 1,3-bis-(2,4-diaminophenoxy)propane | — | — | — | — | 0.051 |
| Color | terracotta | grenadine red | cyclamen | deep black | medium brown |

| Dye Compound/Example | 57 | 58 | 59 | 60 |
|---|---|---|---|---|
| 2-hydroxyethyl-1,4-diaminobenzene | 0.204 | 1.178 | 1.798 | 1.204 |
| 4-amino-3-methylphenol | — | — | — | 2.996 |
| 2-amino-5-methylphenol | — | 0.021 | — | — |
| 4-chlororesorcinol | — | 0.626 | 0.062 | — |
| 2-methylresorcinol | — | 0.048 | 0.804 | 0.756 |
| 5-amino-2-methylphenol | 0.102 | — | 0.053 | 2.504 |
| 2-(2,4-diaminophenoxy)-ethanol | — | — | — | 0.611 |
| 2-amino-6-chloro-4-nitrophenol | — | 0.021 | 0.143 | — |

TABLE 2-continued

DYED HAIR COLOR OBTAINED WITH DYE COMPOSITIONS ACCORDING TO THE INVENTION

| | | | | |
|---|---|---|---|---|
| 3-nitro-4-(3-hydroxypropylamino)phenol | — | — | — | 0.403 |
| 2,4-dinitro-6-(2-hydroxyethyl)phenol | 1.092 | — | — | — |
| Color | mahogany-copper | medium blond | chocolate brown | mahogany |

| Dye Compound/Example | 61 | 62 | 63 | 64 |
|---|---|---|---|---|
| 2,5-diaminotoluene | 2.397 | 0.162 | 3.521 | — |
| 1,4-diaminobenzene | — | — | — | 1.107 |
| 2,3,4,6-tetraamino-pyrimidine | — | — | — | 1.311 |
| 4,5-diamino-1-(2-hydroxyethyl)pyrazole | — | 1.508 | — | — |
| 1,3-diaminobenzene | 0.245 | — | — | — |
| 4-chlororesorcinol | — | — | 1.508 | — |
| resorcinol | — | — | 0.698 | 1.212 |
| 3-aminophenol | — | 0.396 | — | — |
| 5-amino-2-methylphenol | — | 0.212 | — | — |
| 2-amino-4-(2-hydroxyethyl)aminoanisole | 0.621 | 0.476 | 0.447 | — |
| 1-naphthol | — | — | — | 0.821 |
| 2-(2,4-diaminophenoxy)-ethanol | 0.533 | — | 0.482 | — |
| 1,5-bis-(2-hydroxyethoxy)2,4-diaminobenzol | 0.471 | — | 0.379 | — |
| 1,3-bis-(2,4-diaminophenoxy)propane | 0.375 | — | 0.524 | — |
| Color | blue-black | cyclamen | blue-black | black-brown |

Example 65

| | |
|---|---|
| 17.0 g | hydroxypropylcellulose |
| 12.8 g | calcium peroxide |
| 10.3 g | sodium sulfate |
| 10.0 g | ammonium chloride |
| 10.0 g | magnesium carbonate |
| 10.0 g | citric acid |
| 5.0 g | sodium sulfite |
| 5.0 g | silicon dioxide |
| 4.8 g | calcium hydroxide |
| 3.3 g | 1,4-diaminobenzene |
| 2.0 g | sodiuin lauryl sulfate |
| 2.0 g | disodium EDTA |
| 2.8 g | 2-ainino-(2-hydroxyethyl) aminoanisole |
| 2.4 g | calcium carbonate |
| 1.5 g | 4-aminophenol hydrochloride |
| 1.1 g | resorcinol |
| 100.0 g | |

11 g of this dye composition were mixed thoroughly with 89 ml immediately prior to use. The ready-to-use dye preparation so obtained is allowed to act on blond natural hair for 30 minutes at 40° C. Subsequently the hair is thoroughly rinsed with water and dried. The hair has an intense blue-black color.

All percentages in the present application are percentages by weight, unless otherwise indicated.

When it is stated in the following claims and also in the above paragraphs that a concentration range is "based on a ready-to-use dye preparation or composition" it means that the concentration range explicitly stated in the claims or specification is the concentration range in a ready-to-use dye preparation made from the claimed or stated composition (particularly when the claimed composition is an oxidizing agent composition and the ready-to-use dye composition or preparation is made by mixing the oxidizing agent composition with a composition containing developer and coupler substances).

While the invention has been illustrated and described as embodied in a composition for oxidative dyeing of hair and method of using same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A nonaqueous composition for oxidative dyeing of hair, said nonaqueous composition being mixed with water to form a ready-to-use dye preparation before applying said ready-to-use dye preparation to the hair, wherein said nonaqueous composition contains from 0.01 to 25 percent by weight, based on a total amount of said ready-to-use dye preparation, of at least one peroxide selected from the group consisting of magnesium peroxide, calcium peroxide, barium peroxide and strontium peroxide;

from 0.02 to 20 percent by weight, based on said total amount of said ready-to-use dye preparation, of oxidation dye pre-cursor compounds, said oxidation dye pre-cursor compounds consisting of primary aromatic amines having a free hydroxy substituent, a substituted hydroxy group substituent or an amino group substituent in an ortho- or para-position, substituted or unsubstituted m-diaminobenzenes, substituted or unsubstituted m-aminophenols, substituted or unsubstituted resorcinols, naphthols, substituted pyridines, substituted pyrimidines and/or substituted pyrazoles; and from 0.1 to 25 percent by weight, based on said total amount of said ready-to-use dye preparation, of at least one inorganic or organic acid and/or at least one salt thereof.

2. The composition as defined in claim 1, wherein said at least one inorganic or organic acid is selected from the group consisting of hydrochloric acid, sulfuric acid, phosphoric acid, monocarboxylic acids, dicarboxylic acids, polycarboxylic acids, sulfonic acids, aminoacids, aminopolycarboxylic acids, aminosulfonic acids, phosphonic acids, hydroxyphosphonic acids, aminophosphonic acids, monohydroxycarboxylic acids and polyhydroxy carboxylic acids.

3. The composition as defined in claim 1, wherein said at least one inorganic or organic acid is at least one member selected from the group consisting of malic acid, citric acid and tartaric acid.

4. The composition as defined in claim 1, further comprising at least one direct-dyeing dye compound.

5. The composition as defined in claim 4, wherein said at least one direct-dyeing dye compound is selected from the group consisting of trimethylene dye compounds, aromatic nitro dye compounds, azo dye compounds and anthraquinone dye compounds.

6. The composition as defined in claim 1, wherein said oxidation dye pre-cursor compounds consist of a combination of at least one developer substance and at least one coupler substance, wherein said at least one developer substance consists of 2,3,4,6-tetraaminopyrimidine, 4,5-diamino-1-(2-hydroxyethyl)-pyrazole, 2,5-diaminotoluene, 2-(2-hydroxyethyl)-1,4-diaminobenzene, 1,4-diaminobenzene or mixtures thereof; and wherein said at least one coupler substance consists of 2-amino-4-(2-hydroxy-ethyl)aminoanisole, 2-(2,4-diaminophenoxy)ethanol, 1-naphthol, 2-methylresorcinol, 3-aminophenol, 2-hydroxy-4-aminotoluene, N-(3-dimethylamino)phenylurea, 1,3-diaminobenzene, 4-(2-hydroxyethylamino)-1,2-methylenedioxybenzene or mixtures thereof.

7. A ready-to-use dye preparation for dyeing keratin fibers made by mixing, prior to application to the keratin fibers, water with a powdery dye composition;

wherein said powdery dye composition contains from 0.01 to 25 percent by weight, based on a total amount of said ready-to-use dye preparation, of at least one peroxide selected from the group consisting of magnesium peroxide, calcium peroxide, barium peroxide and strontium peroxide;

from 0.02 to 20 percent by weight, based on said total amount of said ready-to-use dye preparation, of oxidation dye pre-cursor compounds, said oxidation dye pre-cursor compounds consisting of primary aromatic amines having a free hydroxy substituent, a substituted hydroxy group substituent or an amino group substituent in an ortho- or para-position, substituted or unsubstituted m-diaminobenzenes, substituted or unsubstituted m-aminophenols, substituted or unsubstituted resorcinols, naphthols, substituted pyridines, substituted pyrimidines and/or substituted pyrazoles; and from 0.1 to 25 percent by weight, based on said total amount of said ready-to-use dye preparation, of at least one inorganic or organic acid and/or at least one salt thereof.

8. A two-component product for oxidative dyeing of hair, wherein said two-component product comprises a nonaqueous preparation in powder or suspension-form containing from 0.01 to 25 percent by weight, based on a total amount of a ready-to-use dye preparation, of at least one peroxide selected from the group consisting of magnesium peroxide, calcium peroxide, barium peroxide and strontium peroxide, and from 0.1 to 25 percent by weight, based on said total amount of said ready-to-use dye preparation, of at least one inorganic or organic acid and/or salt of said acid, and an aqueous cosmetic preparation containing from 0.02 to 20 percent by weight, based on said total amount of said ready-to-use dye preparation, of oxidation dye precursor compounds consisting of primary aromatic amines having a free hydroxy group substituent, a substituted hydroxy group substituent or an amino group substituent in an ortho- or para-position, substituted or unsubstituted m-diaminobenzenes, substituted or unsubstituted m-aminophenols, substituted or unsubstituted resorcinols, naphthols, substituted pyridines, substituted pyrimidines and/or substituted pyrazoles.

9. A ready-to-use dye preparation for dyeing keratin fibers made by mixing an oxidizing agent composition with a dye pre-cursor-containing composition before application to the keratin fibers;

wherein said dye pre-cursor-containing composition contains from 0.02 to 20 percent by weight, based on a total amount of said ready-to-use dye preparation, of oxidation dye pre-cursor compounds; said oxidation dye pre-cursor compounds consisting of primary aromatic amines having a free hydroxy group substituent, a substituted hydroxy group substituent or an amino group substituent in an ortho- or para-position, substituted or unsubstituted m-diaminobenzenes, substituted or unsubstituted m-aminophenols, substituted or unsubstituted resorcinols, naphthols, substituted pyridines, substituted pyrimidines and/or substituted pyrazoles; and wherein said oxidizing agent composition contains from 0.01 to 25 percent by weight, based on said total amount of the ready-to-use dye preparation, of at least one peroxide selected from the group consisting of magnesium peroxide, calcium peroxide, barium peroxide and strontium peroxide, and from 0.01 to 25 percent by weight, based on said total amount of the ready-to-use dye preparation, of at least one inorganic or organic acids and/or at least one salt thereof.

10. The preparation as defined in claim 9, wherein said oxidation dye pre-cursor compounds cons of a combination of at least one developer substance and at least one coupler substance, and wherein said at least one developer substance consists of 2,3,4,6-tetraaminopyrimidine, 4,5-diamino-1-(2-hydroxyethyl)-pyrazole, 2,5-diaminotoluene, 2-(2-hydroxyethyl)-1,4-diaminobenzene, 1,4-diaminobenzene or mixtures thereof; and wherein said at least one coupler substance consists of 2-amino-4-(2-hydroxy-ethyl)aminoanisole, 2-(2,4-diaminophenoxy)ethanol, 1-naphthol, 2-methylresorcinol, 3-aminophenol, 2-hydroxy-4-aminotoluene, N-(3-dimethylamino)phenylurea, 1,3-diaminobenzene, 4-(2-hydroxyethylamino)-1,2-methylenedioxybenzene or mixtures thereof.

11. A method of dyeing hair, said method comprising the steps of:

a) providing a nonaqueous composition for oxidative dyeing of hair containing from 0.01 to 25 percent by weight, based on a total amount of a ready-to-use dye preparation, of at least one peroxide selected from the group consisting of magnesium peroxide, calcium peroxide, barium peroxide and strontium peroxide, and from 0.02 to 20 percent by weight, based on said total amount of said ready-to-use dye preparation, of oxidation dye pre-cursor compounds consisting of primary aromatic amines having a free hydroxy group substituent, a substituted hydroxy group substituent or an amino group substituent in an ortho- or para-position, substituted or unsubstituted m-diaminobenzenes, substituted or unsubstituted m-aminophenols, substituted or unsubstituted resorcinols, naphthols, substituted pyridines, substituted pyrimidines and/or substituted pyrazoles, and from 0.01 to 25 percent by weight, based on said total amount of said ready-to-use dye preparation, of at least one inorganic or organic acid and/or at least one salt thereof;

b) mixing said composition with water before application to the hair to form said ready-to-use dye preparation;

c) applying said ready-to-use dye preparation to hair to be dyed in an amount sufficient for dyeing the hair;

d) allowing said ready-to-use dye preparation to act on the hair at a temperature of from 10 to 50° C. for from 10 to 60 minutes; and e) after step d), rinsing said ready-to-use dye preparation from the hair.

12. The method as defined in claim 11, wherein in step b) said composition is mixed with said water in a composition-to-water weight ratio of 1:0.5 to 1:20.

13. The method as defined in claim 11, wherein said oxidation dye pre-cursor compounds consist of a combination of at least one developer substance and at least one coupler substance, and wherein said at least one developer substance consists of 2,3,4,6-tetraaminopyrimidine, 4,5-diamino-1-(2-hydroxyethyl)-pyrazole, 2,5-diaminotoluene, 2-(2-hydroxyethyl)-1,4-diaminobenzene, 1,4-diaminobenzene or mixtures thereof; and wherein said at least one coupler substance consists of 2-(2-amino-4-(2-hydroxy-ethyl)aminoanisole, 2,4-diaminophenoxy) ethanol, 1-naphthol, 2-methylresorcinol, 3-aminophenol, 2-hydroxy-4-aminotoluene, N-(3-dimethylamino)phenylurea, 1,3-diaminobenzene, 4-(2-hydroxyethylamino)-1,2-methylenedioxybenzene or mixtures thereof.

* * * * *